(12) United States Patent
Kobayashi et al.

(10) Patent No.: US 7,846,703 B2
(45) Date of Patent: Dec. 7, 2010

(54) METHOD FOR ENHANCING POLYMERASE ACTIVITY

(75) Inventors: Eiji Kobayashi, Shiga (JP); Yuki Ueda, Shiga (JP); Yoshimi Sato, Shiga (JP); Takashi Uemori, Shiga (JP); Hiroyuki Mukai, Shiga (JP); Ikunoshin Kato, Shiga (JP)

(73) Assignee: Takara Bio Inc., Shiga (JP)

( * ) Notice: Subject to any disclaimer, the term of this patent is extended or adjusted under 35 U.S.C. 154(b) by 0 days.

(21) Appl. No.: 11/866,148

(22) Filed: Oct. 2, 2007

(65) Prior Publication Data

US 2008/0096262 A1 Apr. 24, 2008

Related U.S. Application Data

(60) Provisional application No. 60/848,401, filed on Oct. 2, 2006.

(51) Int. Cl.
- *C12N 9/10* (2006.01)
- *C12N 9/96* (2006.01)
- *C07K 14/00* (2006.01)
- *C12Q 1/66* (2006.01)
- *C12P 19/34* (2006.01)

(52) U.S. Cl. .......................... 435/193; 435/6; 435/91.2; 435/188; 530/350

(58) Field of Classification Search ................ None
See application file for complete search history.

(56) References Cited

U.S. PATENT DOCUMENTS 6,242,235 B1 * 6/2001 Shultz et al. ................ 435/194
2003/0134292 A1 * 7/2003 Farchaus, III ................ 435/6
2006/0142234 A1 * 6/2006 Chen et al. ................... 514/44
2006/0269934 A1 * 11/2006 Woudenberg et al. ........ 435/6
2008/0003575 A1 * 1/2008 Michalik et al. ............. 435/6
2008/0145910 A1 * 6/2008 Ward et al. ................. 435/188

FOREIGN PATENT DOCUMENTS

| WO | WO 03106678 A1 * | 12/2003 |
| WO | WO 2006099579 A2 * | 9/2006 |
| WO | WO 2008107473 A1 * | 9/2008 |
| WO | WO 2008152102 A1 * | 12/2008 |

OTHER PUBLICATIONS

PubChem Substance ID 24902134, Jan. 21, 2008 [online], [retrieved on Jan. 16, 2009], retrieved from the Internet: <URL: pubchem.ncbi.nlm.nih.gov/summary/summary.cgi?sid=24902134&loc=ec_rcs>.*

Aldrich catalog No. 463302 for glycolic acid ethoxylate 4-nonylphenyl ether, 2009 [online], [retrieved on Sep. 8, 2009], retrieved from the Internet: <URL: www.sigmaaldrich.com/catalog/ProductDetail.do?D7=0&N5=SEARCH_CONCAT_PNO%7CBRAND_KEY&N4=463302%7CALDRICH&N25=0&QS=ON&F=SPEC>.*

* cited by examiner

*Primary Examiner*—Young J Kim
*Assistant Examiner*—Angela M Bertagna
(74) *Attorney, Agent, or Firm*—Browdy and Neimark, PLLC

(57) ABSTRACT

A polymerase activity is effectively enhanced by adding an anionic surfactant, in particular an anionic surfactant having a polyethoxyl group, to a reaction mixture containing a polymerase.

1 Claim, 3 Drawing Sheets

US 7,846,703 B2

METHOD FOR ENHANCING POLYMERASE ACTIVITY

BACKGROUND OF THE INVENTION

1. Field of the Invention

The present invention relates to a method for enhancing a polymerase activity as well as a composition and a reaction mixture used for said method, which are useful in the field of genetic engineering.

2. Description of Related Art

A polymerase is one of the most important enzymes in the field of genetic engineering. Various additives such as DMSO, glycerol, formamide and poly(ethylene glycol) have been reported to enhance a polymerase activity. A surfactant is also one of additives for enhancing a polymerase activity. It is known that a nonionic surfactant stabilizes a thermostable DNA polymerase (Japanese Patent No. 2719528 (corresponding to U.S. Pat. No. 6,127,155)). Furthermore, it has been reported that a cationic surfactant, polyethoxylated amine, stabilizes a polymerase (Japanese Patent No. 3673175 (corresponding to U.S. Pat. No. 6,242,235)). In this document, it is predicted that high affinity ionic bonds protect a protein from denaturation by other active substances, and it is shown that ionic surfactants stabilize a polymerase better than nonionic surfactants. Specifically, the charged groups on the ionic surfactant electrostatically interact with the charged residues on the surface of the protein, the hydrophobic region in the ionic surfactant hydrophobically binds to the hydrophobic site in the protein, and the protein is protected due to the noncovalent crosslinking action. However, it is feared that a cationic surfactant may interact with an anionic nucleic acid molecule as a substrate for a polymerase to reduce the reactivity of the polymerase, although it depends on the concentration of the added surfactant.

Anionic surfactants such as sodium dodecyl sulfate (SDS), sodium deoxycholate, sodium N-lauroyl sarcosinate are known to inhibit a polymerase activity (Weyant, R. S. et al., Bio Techniques, 1990, Vol. 9, p. 308-309). Such anionic surfactants inhibit a polymerase activity even at low concentrations (e.g., 0.01% of SDS). Thus, if a polymerase reaction mixture is contaminated with an anionic surfactant used in pretreatment such as a nucleic acid extraction step, the polymerase activity is considerably inhibited.

With the progress in genetic engineering techniques, large-scale reading of nucleotide sequences and replication of a large amount of nucleic acid are routinely conducted. The influence of enhancement of a polymerase activity is great even if the degree is low. Thus, an additive that enhances a polymerase activity more effectively than conventional additives has been desired. Furthermore, an additive having an effect that is not brought by conventional additives has also been required.

SUMMARY OF THE INVENTION

The present invention has been made in view of the above-mentioned prior art. The main object of the present invention is to provide a method for enhancing a polymerase activity more effectively.

As a result of intensive studies, the present inventors have found that a polymerase activity can be effectively enhanced by adding an anionic surfactant having a polyethoxyl group to a reaction mixture containing a polymerase. Thus, the present invention has been completed.

The first aspect of the present invention relates to a method for enhancing a polymerase activity, the method comprising adding an anionic surfactant having a polyethoxyl group to a reaction mixture containing a polymerase. According to the first aspect, the anionic surfactant may have a sulfonate group or a carboxylate group. Furthermore, the anionic surfactant may be selected from the group consisting of allyl alcohol 1,2-butoxylate-block-ethoxylate ammonium sulfate, glycolic acid ethoxylate 4-nonylphenyl ether, glycolic acid ethoxylate oleyl ether and poly(ethylene glycol)4-nonylphenyl 3-sulfopropyl ether as well as salts thereof.

The second aspect of the present invention relates to a composition comprising a polymerase and an anionic surfactant having a polyethoxyl group. According to the second aspect, the anionic surfactant may have a sulfonate group or a carboxylate group. Furthermore, the anionic surfactant may be selected from the group consisting of allyl alcohol 1,2-butoxylate-block-ethoxylate ammonium sulfate, glycolic acid ethoxylate 4-nonylphenyl ether, glycolic acid ethoxylate oleyl ether and poly(ethylene glycol)4-nonylphenyl 3-sulfopropyl ether as well as salts thereof.

A polymerase activity can be enhanced more effectively using the method and the composition of the present invention.

DETAILED DESCRIPTION OF THE INVENTION

Figure 1:
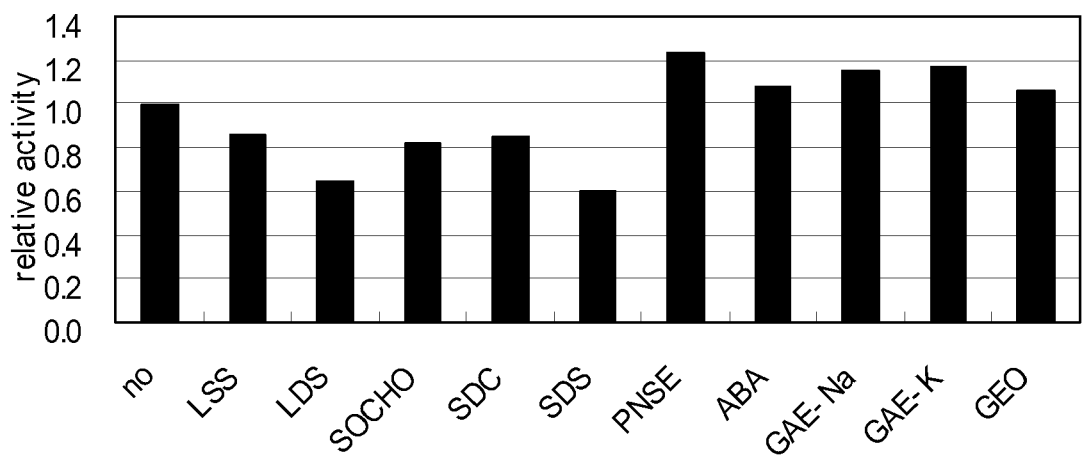
FIG. 1 shows the effect of the method of the present invention.

As used herein, "a polymerase" is an enzyme that extends a nucleic acid strand. It attaches a deoxyribonucleoside triphosphate (dNTP) or a ribonucleoside triphosphate (NTP) to a 3' end of a nucleic acid strand (polymerizes) to synthesize a nucleic acid strand into which the corresponding nucleoside monophosphate is incorporated. Polymerases include DNA-dependent DNA polymerases, RNA-dependent DNA polymerases and DNA-dependent RNA polymerases.

As used herein, "a polymerase activity" means an activity of attaching a deoxyribonucleoside triphosphate or a ribonucleoside triphosphate to a nucleic acid strand to synthesize a nucleic acid strand into which the corresponding nucleoside monophosphate is incorporated, i.e., an activity of catalyzing extension of a nucleic acid.

As used herein, "enhancement of a polymerase activity" means increase in an enzymatic activity of a polymerase. Specifically, enhancement of a polymerase activity means: increase in an activity of incorporating a nucleoside monophosphate into a nucleic acid by a polymerase; increase in an amplification product generated by a polymerase chain reaction (PCR); increase in a length of a nucleic acid strand extended by a polymerase; or increase in accuracy of an incorporated nucleoside triphosphate (dNTP or NTP). Enhancement of a polymerase activity according to the present invention also includes increase in an enzymatic activity of a polymerase by stabilizing a polymerase protein. Furthermore, enhancement of a polymerase activity according to the present invention includes increase in a polymerization activity of a polymerase by suppressing an action of inhibiting a polymerase activity by a contaminant or the like.

As used herein, "a surfactant" is a compound having both a hydrophobic part and a hydrophilic part in a single molecule. It gathers on a boundary between oil and water or between air and water and reduces the boundary tension to stabilize the boundary. "An anionic surfactant" is a surfactant that is dissociated in an aqueous solution into an ion, and of which the atomic group exerting the surface activity forms an anion. "A cationic surfactant" is a surfactant that is dissociated in an aqueous solution into an ion, and of which the atomic group exerting the surface activity forms a cation.

1. Method for Enhancing Polymerase Activity

The present invention provides a method for enhancing a polymerase activity, comprising adding an anionic surfactant having a polyethoxyl group to a reaction mixture containing a polymerase.

There is no specific limitation concerning the anionic surfactant to be added as long as it has a polyethoxyl group (polyoxyethylene group) and enhances a polymerase activity. A polyethoxyl group (polyoxyethylene group) has a structure in which an ethoxyl group (oxyethylene group) is repeatedly connected. It may be a polyethoxyl group having a structure in which for example 1 or more, preferably 1 to 40, more preferably 2 to 25, still more preferably 7 to 20 ethoxyl groups are polymerized. A polyethoxyl group is represented by a chemical formula $(CH_2CH_2O)_n$, wherein n is 1 or more, preferably 1 to 40, more preferably 2 to 25. An anionic surfactant in which a polyethoxyl group is located between a hydrophilic part and a hydrophobic part of the surfactant can be used according to the present invention.

A surfactant having a sulfonate group, a carboxylate group or a phosphate group, which forms an anion in an aqueous solution, as the hydrophilic part of the anionic surfactant can be preferably used according to the present invention. There is no specific limitation concerning the hydrophobic part of an anionic surfactant used according to the present invention. It may be a linear or branched hydrocarbon or it may contain an aromatic ring.

For example, the anionic surfactant used according to the present invention may be represented by the following general formula:

$$R_1-R_2-(CH_2CH_2O)_n-R_3-R_4 \quad \text{(Formula)}$$

wherein one of $R_1$ and $R_4$ is a hydrophobic group and the other is a hydrophilic group. The hydrophobic groups include linear, branched and cyclic hydrocarbons. The hydrocarbons include both saturated and unsaturated ones. The hydrophilic group is a group that forms an anionic ion in an aqueous solution. $R_2$ and $R_3$ are linkers that may be optionally included and may be, for example, $-(CH_2)_m-$ or $-O-(CH_2)_m-$ n is 1 or more, preferably 1 to 40, more preferably 2 to 25. m is 0 or more, preferably 0 to 3.

Examples of anionic surfactants used according to the present invention include allyl alcohol 1,2-butoxylate-block-ethoxylate ammonium sulfate, glycolic acid ethoxylate 4-nonylphenyl ether, glycolic acid ethoxylate oleyl ether and poly(ethylene glycol)4-nonylphenyl 3-sulfopropyl ether or salts thereof as shown in Table 1 below. For example, the salt may be a sodium salt, a potassium salt, an ammonium salt, a lithium salt, a magnesium salt or a calcium salt.

TABLE 1

$$H_2C=CHCH_2O-(CH_2CHO)_x-(CH_2CH_2O)_y-S-ONH_2$$
with $CH_3CH_2$ branch and $=O, =O$ on S Allyl alcohol 1,2-butoxylate-block-ethoxylate ammonium sulfate $$C_9H_{19}-\text{(phenyl)}-O(CH_2CH_2O)_nCH_2-C(=O)-OH$$

n ~ 7
Glycolic acid ethoxylate 4-nonylphenyl ether $$CH_3(CH_2)_xO(CH_2CH_2O)_yCH_2-C(=O)-OH$$

x = 11 - 13
Glycolic acid ethoxylate oleyl ether

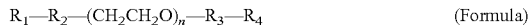

$$C_9H_{19}-\text{(phenyl)}-OCH_2CH_2-OCH_2CH_2CH_2-S(=O)(=O)-OK$$

n ~ 20
Poly(ethylene glycol)4-nonylphenyl 3-sulfopropyl ether potassium salt

One anionic surfactant having a polyethoxyl group or a mixture of plural (preferably two or three) kinds of anionic surfactants each having a polyethoxyl group may be added according to the method of the present invention.

The concentration of an anionic surfactant having a polyethoxyl group according to the method of the present invention may be appropriately selected to enhance a polymerase activity. The surfactant is added at a concentration of generally 10% to 0.0001%, preferably 1% to 0.001%, more preferably 0.1% to 0.01%. In cases where plural kinds of anionic surfactants are used, they are added so that the final concentration of the anionic surfactants (the sum of the concentrations of the anionic surfactants to be used) falls within the above-mentioned concentration range.

The method for enhancing a polymerase activity of the present invention can be applied to a reaction mixture containing a DNA-dependent DNA polymerase, an RNA-dependent DNA polymerase or a DNA-dependent RNA polymerase. There is no specific limitation concerning the DNA polymerase to which the method of the present invention is applied. Examples thereof include pol I-type (pol I-like) DNA polymerases (*Escherichia coli* DNA polymerase I, Klenow fragment, *Thermus aquaticus*-derived DNA polymerase (Taq polymerase), *Thermus filiformis*-derived thermostable DNA polymerase (Tfi DNA polymerase), etc.), α-type (α-like) DNA polymerases (*Pyrococcus furiosus*-derived α-type (α-like) DNA polymerase, *Thermococcus litralis*-derived DNA polymerase (VENT DNA polymerase), *Pyrococcus* sp.-derived DNA polymerase (Pyrobest (registered trademark) DNA polymerase (Takara Bio), KOD DNA polymerase), *Pyrococcus* sp. GB-D-derived DNA polymerase (DEEP VENT DNA polymerase), the DNA polymerases disclosed in WO 2005/118815, PrimeSTAR (registered trademark) HS DNA polymerase (Takara Bio), etc.), and non-α, non-pol I-type DNA polymerases which do not belong to the above. The pol I-type DNA polymerase or the α-type DNA polymerase refers to a group of enzymes classified based on the amino acid sequence homology. The features of the amino acid sequences are described in Nucleic Acids Research, Vol. 15, p. 4045-4057 (1991). The origin of the DNA polymerase may be a prokaryote (e.g., a bacterium or an archaebacterium), a eukaryote, a phage or a virus. In general, an α-type (α-like) DNA polymerase has a 3'-5' exonuclease activity. The DNA polymerase used according to the present invention may or may not have a 3'-5' exonuclease activity. A polymerase activity can be enhanced according to the method of the present invention not only in cases where the polymerase is used alone but also in cases where a mixture of plural DNA polymerases is used.

An RNA-dependent DNA polymerase is called a reverse transcriptase. The present invention can be applied to a reaction mixture containing AMV (avian myeloblastosis virus)- or MMLV (Moloney murine leukemia virus)-derived reverse transcriptase or the like.

A DNA-dependent RNA polymerase is usually called an RNA polymerase. The present invention can be applied to a reaction mixture containing an RNA polymerase derived from a phage (e.g., SP6 or T7 RNA polymerase), or an RNA polymerase derived from a mammal (e.g., H1 or U6 RNA polymerase).

The effect of the method for enhancing a polymerase activity of the present invention can be confirmed using the enzymatic activity of the polymerase as an index. For example, a polymerase activity enhanced by the addition of an anionic surfactant can be confirmed as described in Example 1 below by measuring the amount of a nucleoside monophosphate incorporated into a nucleic acid strand per unit time by the action of the polymerase. Furthermore, the amount of an amplified nucleic acid generated according to a nucleic acid amplification method (e.g., PCR) may be measured. A nucleic acid strand generated according to a nucleic acid amplification method (e.g., PCR) may be observed using agarose gel electrophoresis to confirm the effect of amplifying a nucleic acid strand. In addition, the enhancement of a polymerase activity can be confirmed by measuring the length of a nucleic acid strand extended by the polymerase, examining the increase in accuracy of an incorporated nucleic acid, or the like. The method for enhancing a polymerase activity of the present invention includes any method other than the above with which an effect preferable for a polymerase activity is achieved. There is no specific limitation concerning the mode or the conditions of the reaction according to the present invention as long as the enhancement of a polymerase activity is observed. A case where increase in a polymerization activity of a polymerase is observed in a chained nucleic acid amplification method such as PCR (polymerase chain reaction) is particularly useful according to the present invention.

A case is included in the present invention if a polymerase activity is enhanced upon the addition of an anionic surfactant having a polyethoxyl group according to the method of the present invention as compared with the activity without the addition. Enhancement of preferably 5% or more, more preferably 10% or more, sill more preferably 15% or more, most preferably 20% or more is observed.

The method of the present invention is effective particularly if the concentration of a polymerase or the concentration a nucleic acid as a template in a reaction mixture is low.

According to the method of the present invention, a composition in which a polymerase and an anionic surfactant having a polyethoxyl group have been mixed together and stored beforehand may be used, or they may be mixed together immediately before the initiation of a reaction to prepare a reaction mixture.

The method for enhancing a polymerase activity of the present invention is not restricted by the principle of enhancement. It may be considered that a polymerase activity is enhanced, for example, by: acting on a polymerase to increase the catalytic activity; suppressing nonspecific interaction of a polymerase with a template nucleic acid; providing the optimal amount of an enzyme to a template nucleic acid; stabilizing a polymerase protein; suppressing inactivation of a polymerase; acting on a template nucleic acid to maintain its conformation in a state with which a polymerase reaction readily proceeds; or increasing the efficiency of annealing of a primer to a template nucleic acid. However, the present invention is not restricted by such a principle as long as an action preferable for a polymerase activity is consequently achieved.

2. Composition Comprising Polymerase and Anionic Surfactant Having Polyethoxyl Group The composition of the present invention is a composition comprising a polymerase and an anionic surfactant having a polyethoxyl group which is used for the above-mentioned method for enhancing a polymerase activity. The composition of the present invention can be used to enhance a polymerase activity.

The polymerase utilized for the present invention may be produced using genetic engineering techniques, or it may be purified from a naturally-occurring organism. Many polymerases are commercially available and they can also be utilized for the present invention. A surfactant that is not preferable for the application to the present invention which may be contained can be removed utilizing chromatography, salting-out, dialysis or the like.

The composition of the present invention may further comprise a component necessary for a polymerase reaction. For example, the composition may comprise a buffering agent, a nucleic acid that functions as a primer, a deoxyribonucleoside triphosphate, a ribonucleoside triphosphate or the like.

In another embodiment of the present invention, a reaction buffer for a thermostable DNA polymerase as described below can be used. For example, Tris or phosphate may be used as a buffering component. The concentration may range from about 5 to 150 mM, preferably from about 10 to 100 mM, and the pH at 25° C. may be about 7.0 to 10.0, preferably about 8.0 to 9.0. $K^+$ or $Na^+$ can be used as a monovalent salt. The concentration may range from about 1 to 20 mM, preferably from 2 to 10 mM. $Mg^{2+}$, $Mn^{2+}$ or $Co^{2+}$ can be used as a divalent cation. The concentration may range from about 1.0 to 20.0 mM. The concentration of each dNTP may range from about 0.05 to 2.0 mM, preferably from about 0.1 to 1.0 mM.

In another embodiment of the present invention, a reaction buffer for T4 DNA polymerase as described below can be used. For example, Tris or phosphate may be used as a buffering component. The concentration may range from about 5 to 150 mM, preferably from about 10 to 100 mM, and the pH at 25° C. may be about 7.0 to 9.0, preferably about 7.5 to 8.5. $K^+$ or $Na^+$ can be used as a monovalent salt. The concentration may range from about 10 to 100 mM, preferably from 30 to 70 mM. $Mg^{2+}$, $Mn^{2+}$ or $Co^{2+}$ can be used as a divalent cation. The concentration may range from about 1.0 to 20.0 mM. For example, DTT may be used as a reducing agent. The concentration may be about 0.1 to 5 mM, preferably about 0.3 to 1 mM. The concentration of each dNTP may range from about 0.05 to 2.0 mM, preferably from about 0.1 to 1.0 mM.

EXAMPLES

The following Examples illustrate the present invention in more detail, but are not to be construed to limit the scope thereof.

Among the procedures described herein, basic procedures were carried out as described in J. Sambrook et al. (eds.), Molecular Cloning: A Laboratory Manual 3rd ed., 2001, Cold Spring Harbor Laboratory.

Referential Example 1

A synthetic gene of SEQ ID NO:1 encoding Tfi DNA polymerase was prepared based on the information about the sequence of a thermostable DNA polymerase from *Thermus filiformis* (Tfi DNA polymerase) (accession no. AF030320) with genetic modification for optimal expression in *Escherichia coli*. The synthetic gene of SEQ ID NO:1 was cloned at the HincII site in pUC18. An about 2.5-kbp DNA fragment obtained by treatment with BspHI and BamHI was cloned between the NcoI and BamHI sites in an expression vector pTV118N. The thus obtained vector for expressing Tfi DNA polymerase was used to transform *Escherichia coli* JM109, the resulting transformant was cultured, and the cells were collected by centrifugation and then disrupted by sonication. A supernatant obtained by centrifuging the cell homogenate was subjected to nucleic acid removal using polyethyleneimine and heating followed by column purification using phenyl-Sepharose, heparin-Sepharose and HiTrapQ in this order. A fraction containing Tfi DNA polymerase at a high concentration obtained as a result of the procedure was dialyzed and then subjected to exchange with a surfactant-free configuration buffer (20 mM Tris-HCl (pH 8.0), 100 mM KCl, 0.1 mM EDTA, 1 mM DTT, 50% glycerol).

Example 1

Preparation of Sample

In this Example, the activity of Tfi DNA polymerase was measured as follows.

Briefly, a sample to be subjected to activity measurement was reacted at 75° C. for 5 minutes in 50 μl of a reaction mixture for activity measurement (18 mM Tris-hydrochloride buffer (pH 9.0), 13.5 mM magnesium chloride, 1.8 mM 2-mercaptoethanol, 36 μM each of dATP, dGTP, dCTP and dTTP, 9 μCi/ml of [$^3$H]-methyl TTP, 0.18 mg/ml of active-type salmon sperm DNA).

After reaction, 40 μl of the reaction mixture was spotted onto DE81 paper (Whatman). The paper was washed four times with 5% Na$_2$PO$_4$ followed by water and ethanol.

After drying, the radioactivity remaining on DE81 paper was measured using a liquid scintillation counter. An amount of the enzyme that incorporated 10 nmol of [$^3$H]-methyl TMP into DNA in 30 minutes according to the above-mentioned enzymatic activity measurement method was defined as 1 U of the enzyme.

Example 2

One of the anionic surfactants as shown in Table 2 was added to surfactant-free Tfi DNA polymerase (containing 0.1% bovine serum albumin) at a final concentration of 0.5% and the activity was measured according to the method as described in Example 1.

TABLE 2

| Sample number | Abbreviation | Surfactant |
|---|---|---|
| 1 | LSS | N-Lauroylsarcosine-sodium salt |
| 2 | LDS | Lithium dodecyl sulfate |
| 3 | SOCHO | Sodium cholate |
| 4 | SDC | Sodium deoxycholate |
| 5 | SDS | Sodium dodecyl sulfate |
| 6 | PNSE | Poly(ethylene glycol)4-nonylphenyl 3-sulfopropyl ether potassium salt |
| 7 | ABA | Allyl alcohol 1,2-butoxylate-block-ethoxylate, ammonium sulfate end-capped solution |
| 8 | GAE-Na | Glycolic acid ethoxylate 4-nonylphenyl ether sodium salt |
| 9 | GAE-K | Glycolic acid ethoxylate 4-nonylphenyl ether potassium salt |
| 10 | GEO | Glycolic acid ethoxylate oleyl ether |

The measurement results are shown in FIG. 1. In FIG. 1, the longitudinal axis represents the relative activity defining the activity without the addition of surfactant as 1. The horizontal axis represents the surfactant with the abbreviation as shown in Table 2. The anionic surfactants of sample numbers 6 to 10 enhanced the Tfi DNA polymerase activity, whereas the anionic surfactants of sample numbers 1 to 5 inhibited the same. Thus, it was shown that the surfactants of sample numbers 6 to 10 enhanced the polymerase activity.

Example 3

Figure 2:
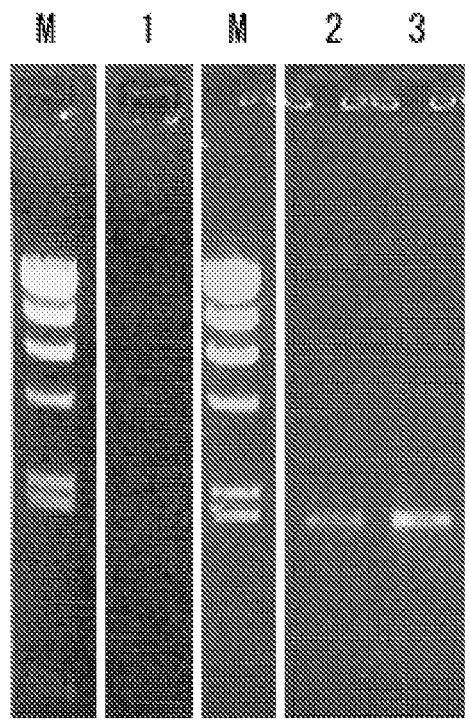
FIG. 2 shows the effect of the method of the present invention.

The effect of enhancing an activity of Tfi DNA polymerase by an anionic surfactant, poly(ethylene glycol) 4-nonylphenyl 3-sulfopropyl ether potassium salt (PNSE), was examined using a reaction of amplifying human DCLRE1A gene by PCR. The PCR reaction was conducted using synthetic DNA primers having nucleotide sequences of SEQ ID NOS:2 and 3 for amplifying a 2-kbp DNA fragment from human DCLRE1A gene as primers for an amplification reaction in a reaction system of a total volume of 50 μL containing 50 mM Tris-HCl (pH 8.4), 15 mM (NH$_4$)$_2$SO$_4$, 5 mM KCl, 0.2 mM each of dNTPs, 1.5 mM MgCl$_2$, 0.2 μM each of synthetic DNA primers of SEQ ID NOS:2 and 3, 1.25 units of Tfi DNA polymerase (in surfactant-free configuration buffer) and 100 ng of human genomic DNA as a template. PNSE was added to the reaction system at a final concentration of 0, 0.01 or 0.1%. A PCR reaction was conducted using Thermal Cycler DICE (Takara Bio) under the following PCR conditions: 94° C. for 2 minutes; 30 cycles of 94° C. for 30 seconds, 60° C. for 30 seconds and 68° C. for 2 minutes; and finally 68° C. for 10 minutes. After reaction, 3 μL each of the reaction mixtures was subjected to electrophoresis on 1% LO3 agarose (Takara Bio). The results are shown in FIG. 2. Specifically, FIG. 2 shows results of PCR amplification of human DCLRE1A gene from human genomic DNA. Lane M: molecular weight marker; Lanes 1 to 3: results of amplification with the addition of PNSE at final concentrations of 0, 0.1 and 0.01%, respectively. Based on the results in FIG. 2, the effect of enhancing the Tfi DNA polymerase activity by PNSE was confirmed.

Example 4

Figure 3:
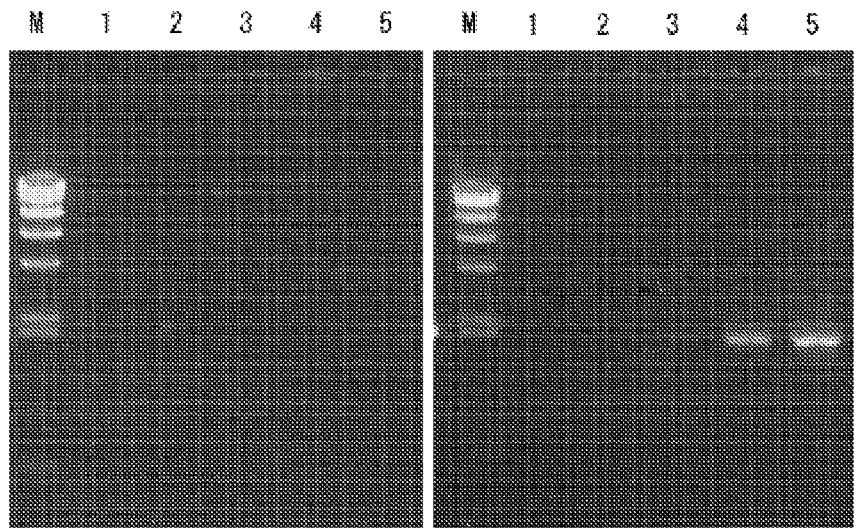
FIG. 3 shows the effect of the method of the present invention.

The effect of enhancing an activity of PrimeSTAR (registered trademark) HS DNA polymerase by an anionic surfactant, PNSE, was examined using a DNA amplification reaction with λ phage genomic DNA as a template by PCR. A surfactant had been removed from the polymerase using Q-Sepharose column chromatography before use. Furthermore, a DNA polymerase sample in which PNSE was added at a final concentration of 0.2% following the above procedure was also prepared. The PCR reaction was conducted using synthetic DNA primers having nucleotide sequences of SEQ ID NOS:4 and 5 for amplifying a 2-kbp DNA fragment from λ phage genomic DNA as primers for an amplification reaction in a reaction system of a total volume of 50 μL containing 1× PrimeSTAR Buffer (Takara Bio), 0.2 mM dNTP mix, 0.2 μM each of synthetic DNA primers of SEQ ID NOS:4 and 5, 0.25 unit of PrimeSTAR HS DNA polymerase (without a surfactant or with the addition of 0.2% PNSE) and 0.1, 1, 10 or 100 pg of λ phage genomic DNA as a template. A PCR reaction was conducted using Thermal Cycler DICE (Takara Bio) under the following PCR conditions: 30 cycles of 98° C. for 10 seconds, 60° C. for 5 seconds and 72° C. for 2 minutes. After reaction, 3 μL each of the reaction mixtures was subjected to electrophoresis on 1% LO3 agarose (Takara Bio). The results are shown in FIGS. 3A and 3B. Specifically, FIGS. 3A and 3B show results of PCR reactions using λ phage genomic DNA as a template and PrimeSTAR HS DNA polymerase with or without 0.2% PNSE in the configuration buffer. Lane M: molecular weight marker; Lanes 1 to 5: results of reactions using 0, 0.1, 1, 10 and 100 pg of λ phage genomic DNA as a template, respectively. Based on the results in FIGS. 3A and 3B, the effect of enhancing the PrimeSTAR HS DNA polymerase activity by PNSE was confirmed.

Example 5

Figure 4:
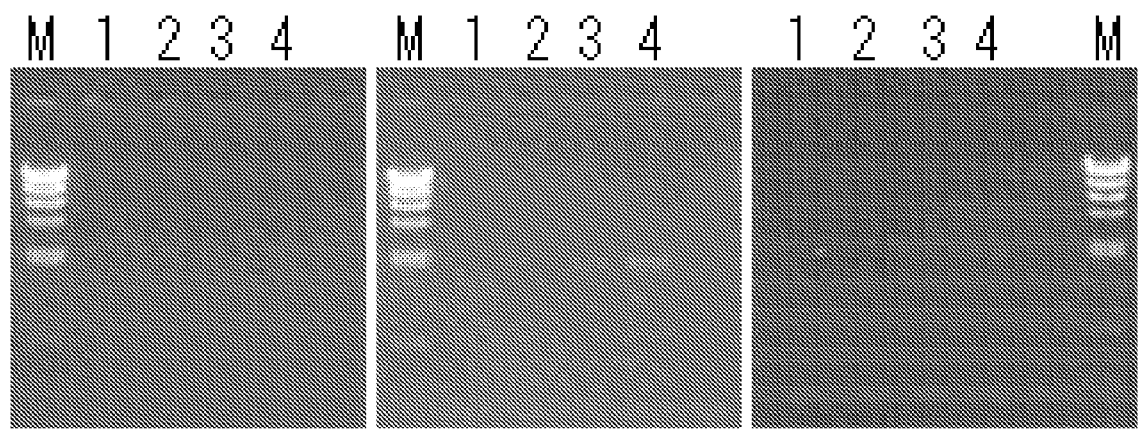
FIG. 4 shows the effect of the method of the present invention.

The effect of enhancing an activity of Pyrobest (registered trademark) DNA polymerase by an anionic surfactant, PNSE, and a nonionic surfactant, Triton X-100, was examined using a reaction of amplifying human DCLRE1A gene by PCR. The PCR reaction was conducted using synthetic DNA primers having nucleotide sequences of SEQ ID NOS:2 and 3 for amplifying a 2-kbp DNA fragment from human DCLRE1A gene as primers for an amplification reaction in a reaction system of a total volume of 50 μL containing 120 mM Tris-acetate (pH 8.5), 6 mM $(NH_4)_2SO_4$, 10 mM KOAc, 0.2 mM each of dNTPs, 1 mM $Mg(OAc)_2$, 0.01% BSA, 0.2 μM each of synthetic DNA primers of SEQ ID NOS:2 and 3, 0.5 U of Pyrobest DNA polymerase (Takara Bio) from which the surfactant had been removed by loading onto heparin-Sepharose column chromatography followed by Q-Sepharose column chromatography and 0.1, 1 or 10 ng of human genomic DNA as a template. PNSE or Triton X-100 (Nacalai Tesque) was added to the reaction system at a final concentration of 0 or 0.005%. A PCR reaction was conducted using Thermal Cycler DICE (Takara Bio) under the following PCR conditions: 30 cycles of 98° C. for 10 seconds and 68° C. for 2 minutes. After reaction, 3 μL each of the reaction mixtures was subjected to electrophoresis on 1% LO3 agarose (Takara Bio). The results are shown in FIG. 4. FIGS. 4A, 4B and 4C show results of PCR reactions using human genomic DNA as a template without a surfactant, with 0.005% PNSE or with 0.005% Triton X-100 in the PCR reaction mixtures. Specifically, FIG. 4 shows results of PCR amplification of human DCLRE1A gene from human genomic DNA. Lane M: molecular weight marker; Lanes 1 to 4: results of PCR reactions using 0, 0.1, 1 and 10 ng of human genomic DNA as a template, respectively. Based on the results in FIGS. 4A and 4B, the effect of enhancing the Pyrobest DNA polymerase activity by PNSE was confirmed. Furthermore, it was confirmed based on the results of FIGS. 4B and 4C that the effect of enhancing the Pyrobest DNA polymerase activity by 0.005% PNSE was higher than that by 0.005% Triton X-100.

Example 6

Figure 5:
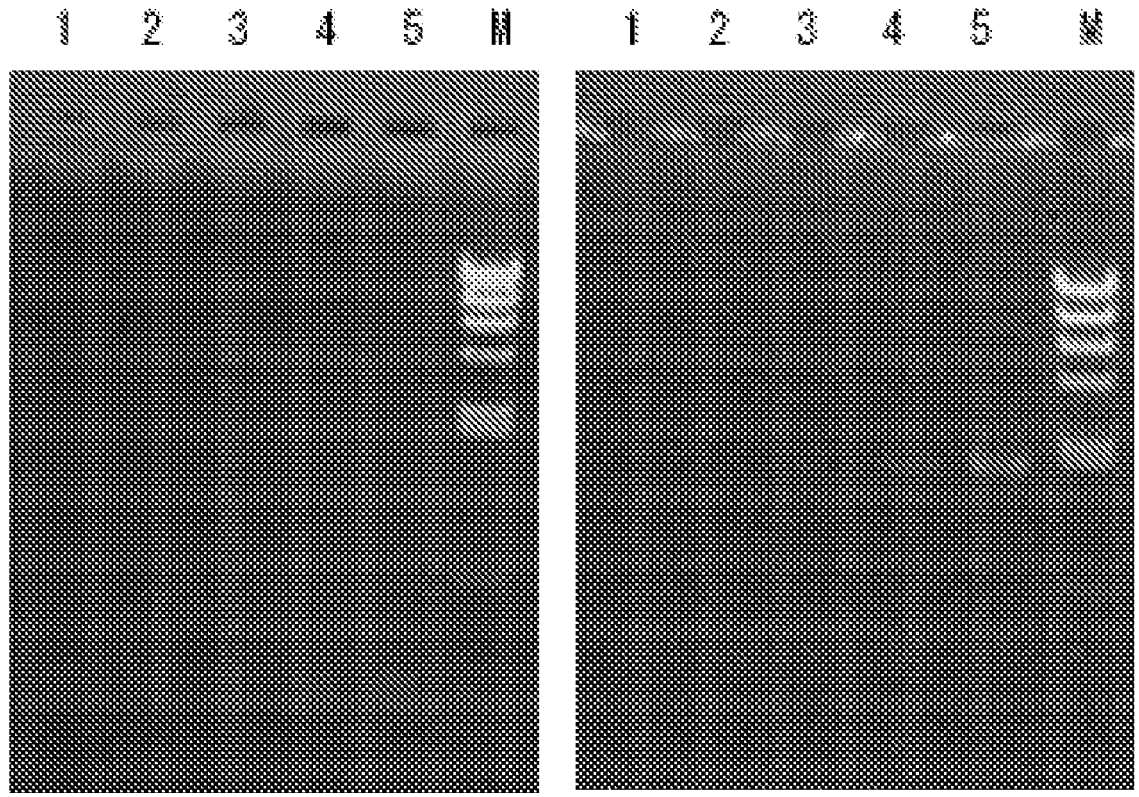
FIG. 5 shows the effect of the method of the present invention.

The effect of enhancing an activity of Advantage GC polymerase mix (a mixture of two DNA polymerases) by an anionic surfactant, PNSE, was examined using a reaction of amplifying human DCLRE1A gene by PCR. The PCR reaction was conducted using synthetic DNA primers having nucleotide sequences of SEQ ID NOS:2 and 3 for amplifying a 2-kbp DNA fragment from human DCLRE1A gene as primers for an amplification reaction in a reaction system of a total volume of 25 μL containing 1× TITANIUM (trademark) Taq PCR Buffer (Clontech), 0.2 mM each of dNTPs, 0.4 μM each of synthetic DNA primers of SEQ ID NOS:2 and 3, ×0.2 (one fifth of usually used amount) Advantage GC polymerase mix (Clontech) and 0.05, 0.5, 5 or 50 ng of human genomic DNA as a template. PNSE was added to the reaction system at a final concentration of 0 or 0.01%. A PCR reaction was conducted using Thermal Cycler DICE (Takara Bio) under the following PCR conditions: 95° C. for 1 minute; 30 cycles of 95° C. for 30 seconds and 68° C. for 2 minutes; and 68° C. for 3 minutes. After reaction, 3 μL each of the reaction mixtures was subjected to electrophoresis on 1% LO3 agarose (Takara Bio). The results are shown in FIG. 5. FIGS. 5A and 5B show results of PCR reactions using human genomic DNA as a template with or without 0.01% PNSE in the PCR reaction mixtures. Specifically, FIG. 5 shows results of PCR amplification of human DCLRE1A gene from human genomic DNA. Lane M: molecular weight marker; Lanes 1 to 5: results of PCR reactions using 0, 0.05, 0.5, 5 and 50 ng of human genomic DNA as a template, respectively. Based on the results in FIGS. 5A and 5B, the effect of enhancing the Advantage GC polymerase mix activity by PNSE was confirmed.

The present invention provides a method for enhancing a polymerase activity. The present invention further provides a composition with an enhanced polymerase activity. The present invention is a technique that can be widely applied to nucleic acid amplification, nucleotide sequence reading and the like in the field of genetic engineering, and can be used to increase the operation efficiency.

All publications and patent documents cited herein are hereby incorporated by reference in their entity for all purposes to the same extent as if each were so individually denoted.

Sequence Listing Free Text

SEQ ID NO:1: DNA fragment containing DNA polymerase gene from *Thermus filiformis*

SEQ ID NO:2: Synthetic primer for amplification of human DCLRE1A gene.

SEQ ID NO:3: Synthetic primer for amplification of human DCLRE1A gene.

SEQ ID NO:4: Synthetic primer for amplification of lambda phage.

SEQ ID NO:5: Synthetic primer for amplification of lambda phage.

What is claimed is:

1. A composition comprising a polymerase and an anionic surfactant,
wherein the anionic surfactant is selected from the group consisting of allyl alcohol 1,2-butoxylate-block-ethoxylate ammonium sulfate, and poly(ethylene glycol)4-nonylphenyl 3-sulfopropyl ether as well as salts thereof, and
wherein the concentration of the anionic surfactant is 0.001% to 1%.

* * * * *

SEQUENCE LISTING

<160> NUMBER OF SEQ ID NOS: 5

<210> SEQ ID NO 1
<211> LENGTH: 2526
<212> TYPE: DNA
<213> ORGANISM: Artificial Sequence
<220> FEATURE:
<223> OTHER INFORMATION: DNA fragment containing DNA polymerase gene
      from Thermus filiformis

<400> SEQUENCE: 1

```
catatgatca tgaccccact gtttgatctg gaggaaccgc cgaaacgcgt gctgctggtg      60
gatggccacc acctggccta tcgcaccttc tatgccctga ccctcaccac ctcgcgtggt     120
gagccggtgc agatggtcta tggcttcgca cgcagcctcc tcaaagcctt gaaagaggat     180
ggccaggcgg tggtcgtggt ctttgatgcc aaagccccgt cgttccgcca cgaggcctat     240
gaggcctata aagcaggtcg cgcaccgacc ccggaggatt tcccgcgtca gctcgccttg     300
gtcaaacgcc tggtggatct gctgggcctg gtccgcctgg aggcaccggg ctatgaggcg     360
gatgatgtcc tgggcaccct ggccaaaaaa gccgaacgcg agggcatgga ggtgcgcatc     420
ctcacgggcg atcgcgattt cttccagctc ctctcggaga agtctcggt cctcctgccg      480 gatggcaccc tggtcacccc gaaagatgtc caggagaaat atggcgttcc gccggagcgc     540
tgggtggatt ccgcgcact cacgggcgat cgctcggata acatcccggg tgtggcgggt     600
attggcgaga aaaccgccct gcgcctcctc gcagagtggg gcagcgtgga aaacctcctg     660
aaaaacctgg atcgcgtgaa accggattcg ctccgtcgca aaattgaggc gcacctggag     720
gatctccacc tctcgttaga tctggcacgc atccgcaccg atctcccgct ggaggtggat     780
tttaaagccc tgcgccgtcg cacccggat ctggagggcc tgcgtgcctt tttggaggag      840
ctggagttcg gcagcctcct ccacgagttc ggcctcctgg tggcgagaa accgcgtgag      900 gaggcaccgt ggccgccacc ggaaggcgcc ttcgtgggct tcctcctgtc gcgcaaagag     960
ccgatgtggg cggagctgct ggccctggcg gcagcctcgg agggtcgcgt ccaccgcgca    1020
accagcccgg ttgaggccct ggccgatctc aaagaggccc gtggcttcct ggccaaagat    1080
ctggccgttt tggccctgcg cgagggcgtg gcccttgatc cgacggatga tccgctcctg    1140
gtggcctatc tccttgatcc ggccaacacc caccccggagg gcgtggcacg tcgctatggc    1200
ggtgagttca cggaggatgc agcggagcgc gcactcctct cggagcgcct cttccagaac    1260
ctctttccgc gtctgtcgga gaaactcctc tggctctatc aggaagtgga gcgtccgctc    1320
tcgcgcgtct tggcccacat ggaggcccgt ggcgtgcgcc tggatgtccc gctgctggag    1380
gccctctcgt ttgagctgga gaaagagatg gagcgcctgg agggcgaggt cttccgtttg    1440
gcaggtcacc cgttcaacct caactcgcgc gatcagctgg aacgcgtcct ctttgatgag    1500
ctgggcctca cccggtggg tcgcacggag aaaacgggca aacgctcgac cgcccagggt    1560
gccctggagg ccctccgcgg tgcccacccg atcgtggagc tcatcctcca gtatcgcgag    1620
ctgtcgaaac tcaaaagcac ctatcttgat ccgctgccgc gtctcgtcca cccgcgtacg    1680
ggacgcctcc acaccgcctt caaccagacg gccacggcca cggacgcct gtcgagctct    1740 gatccgaacc tgcaaaacat cccggtgcgc acccgttgg ccagcgcat ccgcaaagcc      1800 ttcgtggccg aggagggctg gctcctgttg cagcgggatt attcgcagat tgagctccgc    1860
gtcctggccc acctctcggg cgatgagaac ctgaaacgcg tcttccgcga gggcaaagat    1920
```

-continued

```
atccataccg agaccgcagc ctggatgttc ggcttagatc cggcactggt tgatccgaaa      1980
atgcgtcgcg cagccaaaac ggtcaacttc ggcgtcctct atggcatgtc ggcccaccgc      2040
ctctcgcagg agctcggcat tgattataaa gaggcggagg cctttattga gcgctatttc      2100
cagagcttcc cgaaagtgcg cgcatggatt gaacgcaccc tggaggaggg tcgcacgcgt      2160
ggctatgtgg agaccctgtt cggccgtcgt cgctatgtgc cggatctggc ctcgcgcgtc      2220
cgctcggtgc gcgaggcagc ggagcgcatg gccttcaaca tgccggtgca gggcaccgcc      2280
gcagatctga tgaaaatcgc gatggtcaaa ctcttcccgc gtctgaaacc gctgggcgcc      2340
cacctcctcc tccaagtgca cgatgagctg gtcctggagg tgccggagga tcgtgccgag      2400
gaggccaaag ccctggtcaa agaggtcatg gagaacgcct atccgctgga tgtgccgctc      2460
gaggtggagg tgggcgtggg tcgcgattgg ctggaggcga aacaggattg ataaggatcc      2520
aagctt                                                                2526
```

<210> SEQ ID NO 2
<211> LENGTH: 25
<212> TYPE: DNA
<213> ORGANISM: Artificial Sequence
<220> FEATURE:
<223> OTHER INFORMATION: Synthetic primer for amplification of human
      DCLRE1A gene.

<400> SEQUENCE: 2
ccttatgatc tggcatgtac tggtg                                             25

<210> SEQ ID NO 3
<211> LENGTH: 25
<212> TYPE: DNA
<213> ORGANISM: Artificial Sequence
<220> FEATURE:
<223> OTHER INFORMATION: Synthetic primer for amplification of human
      DCLRE1A gene.

<400> SEQUENCE: 3
attaagtgta ctgactggcg atgtg                                             25

<210> SEQ ID NO 4
<211> LENGTH: 35
<212> TYPE: DNA
<213> ORGANISM: Artificial Sequence
<220> FEATURE:
<223> OTHER INFORMATION: Synthetic primer for amplification of lambda
      phage.

<400> SEQUENCE: 4
gatgagttcg tgtccgtaca actggcgtaa tcatg                                  35

<210> SEQ ID NO 5
<211> LENGTH: 22
<212> TYPE: DNA
<213> ORGANISM: Artificial Sequence
<220> FEATURE:
<223> OTHER INFORMATION: Synthetic primer for amplification of lambda
      phage.

<400> SEQUENCE: 5
gatagctgtc gtcataggac tc                                                22